(12) United States Patent
Carter

(10) Patent No.: US 6,379,919 B1
(45) Date of Patent: Apr. 30, 2002

(54) METHOD FOR ISOLATING THIOCYANATE RESISTANT BACTERIA

(76) Inventor: Andrew J. Carter, 1825 E. Plano Parkway #160, Plano, TX (US) 75074

(*) Notice: Subject to any disclaimer, the term of this patent is extended or adjusted under 35 U.S.C. 154(b) by 0 days.

(21) Appl. No.: 09/578,867

(22) Filed: May 26, 2000

Related U.S. Application Data

(60) Provisional application No. 60/136,777, filed on May 28, 1999.

(51) Int. Cl.7 ................................ C12P 1/04; C12P 3/00
(52) U.S. Cl. ..................... 435/34; 435/29; 435/262; 435/262.5; 423/658.5; 423/1; 75/330
(58) Field of Search .......................... 435/34, 29, 262, 435/262.5; 423/658.5, 1; 75/330

(56) References Cited

U.S. PATENT DOCUMENTS

| | | |
|---|---|---|
| 4,343,773 A | 8/1982 | Miller et al. |
| 4,571,387 A | 2/1986 | Bruynesteyn et al. |
| 4,987,081 A | 1/1991 | Hackl et al. |
| 5,006,320 A | 4/1991 | Reid et al. |
| 5,244,493 A | 9/1993 | Brierley et al. |
| 5,246,486 A | 9/1993 | Brierley et al. |
| 5,332,559 A | 7/1994 | Brierley et al. |
| 5,354,359 A | 10/1994 | Wan et al. |
| 5,431,717 A | 7/1995 | Kohr |
| 5,573,575 A | 11/1996 | Kohr |

FOREIGN PATENT DOCUMENTS

| | | |
|---|---|---|
| CA | 2155050 | 2/1996 |

*Primary Examiner*—Leon B. Lankford, Jr.
(74) *Attorney, Agent, or Firm*—Patton Boggs LLP

(57) ABSTRACT

The present invention relates to microbiological processes for the oxidative treatment of refractory gold and base metal ores and concentrates, and specifically, to bacterial inoculums for use in such processes that are strongly resistant to thiocyanate toxicity. The present invention also relates to methods of developing and using these bacteria. The use of a bacterial inoculum with high thiocyanate resistance confers a number of technological advantages on biooxidation processes including improvements in operating flexibility, operation costs and environmental acceptability.

16 Claims, No Drawings

METHOD FOR ISOLATING THIOCYANATE RESISTANT BACTERIA

This application claims priority of provisional application 60/136,777 filed May 28, 1999 and hereby incorporates the contents of said provisional application by reference.

BACKGROUND OF THE INVENTION

The present invention relates to microbiological processes for the oxidative pretreatment of refractory gold and base metal ores and concentrates, and, more specifically, to novel bacterial cultures and inoculums strongly resistant to thiocyanate toxicity which are useful in such processes. The invention further relates to methods of developing and using these resistant bacterial strains.

Precious metals are found throughout the world as an ore within the Earth's crust on the crust surface and dispersed in bodies of water. The precious metal is nearly always in an unrefined state intimately associated with other minerals such as sulfur in the form of arsenopyrite or pyrite. To extract the metal, ore must be processed to remove contaminating minerals such as sulfur, carbon and iron. A commonly used processing technique is cyanidation which involves, quite simply, leaching the ore with cyanide. The cyanide leaches the ore, releasing the precious metal from its association with the gangue minerals. Released metal leaches into a liquid phase from which it can be recovered.

Gold ores are categorized into two types—free milling and refractory—depending on their refractoriness to cyanidation treatment. Free milling ores generally have a low sulfur content and are most often processed by simple gravity techniques or direct cyanidation. Refractory ores, having a higher sulfur content, are difficult to process due to a high excess content of metallic sulfides, such as pyrite, arsenopyrite and other matter, and require more complex extraction methods. One of the most common of such measures is oxidation.

Oxidation of refractory ores involves a pretreatment step in which the ore is subjected to well-known roasting or pressure-oxidation techniques, typically in conjunction with a pre-concentration process. Increasingly, biooxidation is being used as the pretreatment of choice in substitution of these other more traditional oxidation processes. In biooxidation, the metal sulfides in ore are oxidized in a microbial pretreatment step, prior to the cyanidation step. Specifically, the bacteria oxidize both iron and sulfur under acidic conditions. Oxidation of iron sulfide particles causes the solubilization of iron as ferric ion and sulfide as sulfate ion. This liberates the encapsulated precious metal and makes it amenable to a leaching agent, such as cyanide. The precious metal is subsequently recovered from the oxidized materials by cyanidation, carbon-in-leach of thiosulfate leaching processes.

The adaptation of bacteria in the biooxidation process to recover precious metals from refractory ores has been previously described in a number of variations. For example, one method involves oxidizing multi metallic sulfide ores using a combination of chemical/biological leaching process and at least three different types of bacteria (U.S. Pat. No. 4,987,081). Bacterial cultures of *Thiobacillus thiooxidans, Thiobacillus ferrooxidans* and *Leptospirillum ferrooxidans* are first adapted to high dissolved arsenic concentrations and low pH by subjecting the cultures in a solution containing dissolved arsenic to successive incremental concentrations of arsenic while operating in a continuous mode.

Another process involves the biological oxidation of sulfide in sulfide-containing gold ore followed by cyanide leaching (U.S. Pat. No. 5,006,320). This method involves a further processing step for aerating microorganisms during the oxidation step followed by a subsequent extraction of the metal value from the biooxidized ore.

Biooxidation is not limited to the treatment of gold ores. A related method for producing nickel from sulfide ore involves oxidation by heap leaching (Canadian Patent No. 2,155,050). According to this method, nickel ore, which contains a substantial amount of iron, is subjected to a biological oxidation step and separated from iron into an eluate solution. Nickel is removed from the solution by solvent extraction or by use of an ion exchange resin and subsequent electrowinning of the ferronickel.

Metals can also be recovered from refractory sulfide ores by first separating the crushed ore in to a fines and a coarse fraction (U.S. Pat. No. 5,573,575). A heap is formed from the coarse fraction and a concentrate is produced from the fines. The concentrate is then added to the heap for biooxidation.

Alternatively, biooxidation of sulfides in the mineral ores may be done by forming particulates. A heap of particulates is formed and a leaching solution is circulated within the heap (U.S. Pat. No. 5,246,486). A variation on this technique involves polymer agglomeration to aid in the removal of particulates from the metal ore (U.S. Pat. No. 5,332,559).

Metals can also be recovered from a refractory sulfide ore by first separating the clays and fines from the crushed ore, and forming a heap from the crushed refractory ore (U.S. Pat. No. 5,431,717). If there is a sufficient amount of precious metal in the separated clays and fines, these materials are further processed.

Methods for the biooxidation of refractory carbonaceous or carbonaceous-sulfidic ore material using a specific carbon-deactivating microbial consortium have also been used with varying degrees of success (U.S. Pat. No. 5,244,493).

Preg-robbing by carbon and carbon-containing compounds is also a major problem interfering with efficient recovering of metals from refractory ores. One process to overcome this problem uses leaching with a thiosulfate lixiviant to selectively remove the metal (U.S. Pat. No. 5,354,359). This process involves contacting particulates containing precious metal and preg-robbing carbonaceous components with a thiosulfate lixiviant solution forming stable precious metal thiosulfate complexes. The lixiviant solution is recovered after it has had time to become loaded with the metal in the ore material.

Leaching has also been used to remove copper from copper sulfide-containing ore (U.S. Pat. No. 4,571,387). According to this process, ore is ground and mixed with an aqueous acid-leaching medium containing sulfide-oxidizing bacteria, a bacterial nutrient and a catalytic amount of silver. Carbon dioxide and oxygen are provided as well as a bacterial compatible acid. The basic leaching process has been enhanced to increase the leaching rate of a mineral when the mineral is characterized by the tendency to form a reaction product layer during leaching (U.S. Pat. No. 4,343,773). A particulate modifier such as carbon is mixed with the mineral before leaching and selectively alters the characteristics of the reaction product layer.

Prior to incurring the substantial costs inherent in scaling up to biooxidize a particular ore, the ore under consideration typically is batch tested to determine if it is suitable for biooxidation. However, conventional testing procedures can take as long as six months to complete due to the time needed for adaptation of the bacteria and the lag phase between inoculation and the onset of oxidation.

A number of intermediate oxidation products of sulfur including elemental sulfur, polymeric sulfur, sulfite, thiosulfate and polythionates are generated during biooxidation, particularly if oxidation is incomplete. Many of these compounds will react with cyanide in the gold extraction process to form thiocyanate, which is a major cyanide consumer. If a cyanide destruction process is not incorporated as part of the treatment plant, the thiocyanate is discharged with the process tailings. In conventional gold extraction processes, tailings solution containing thiocyanate is often recycled to the process. However, thiocyanate is toxic to the bacteria employed in biooxidation at relatively low levels of between 5 ppm and 25 ppm.

Thus, in systems utilizing microbial biooxidation as the method for oxidizing the ore, tailings solution cannot currently be recycled upstream of the biooxidation process.

In addition, the need for high quality water in biooxidation places further constraints on the process, both in terms of the requirement for large quantities of fresh water and the inability to re-use tailings solution.

SUMMARY OF THE INVENTION

The present invention overcomes the problems and disadvantages associated with current strategies and designs and provides novel bacterial cultures and inoculums which are resistant to thiocyanate, and, thus, can be used in processes where the bacteria may be exposed to thiocyanate, such as those where tailings solutions are reused. In addition, for materials of specific mineralogical content, the inoculums of this invention may be used to facilitate novel processes involving simultaneous biooxidation and co-extraction of gold using a thiocyanate extraction route.

The present invention relates to bacterial inoculums or cultures that are capable of effectively oxidizing refractory ores while simultaneously being resistant to thiocyanate. The inoculums of this invention prevent collapse of the process during inadvertent use or intentional recycling of tailings solution containing thiocyanate. Such bacteria also allow greater environmental acceptability by permitting re-use of tailings solution, which would have a positive impact on the process water balance and allow cost reductions associated with a reduction of fresh water requirements.

One embodiment of the invention is directed to methods for isolating a thiocyanate-resistant bacterial culture. These methods involve inoculating a tail sample containing a concentration of thiocyanate with a population of biooxidative bacteria; culturing the population in nutrient medium contain a first concentration of solids for a first period of time; increasing the solids concentration of the medium to a second concentration of solids and culturing the population for a second period of time; increasing the solids concentration of the medium to a third concentration of solids and culturing the population for a third period of time; and harvesting the population of bacteria.

Another embodiment of the invention is directed to methods for recovering a metal from a refractory ore. These methods involve biooxidize the ore using the bacteria of the present invention, and leaching the metal in an acidic thiocyanate solution. In a preferred embodiment, the biooxidize and the leaching are performed substantially simultaneously.

A further embodiment of the present invention is directed to bacterial inoculums and cultures that are resistant to thiocyanate and to bacterial inoculums and cultures that are isolated by the methods of this invention.

Other embodiments and advantages of the invention are set forth, in part, in the description which follows and, in part, will be obvious from the description and may be learned from the practice of this invention.

DETAILED DESCRIPTION OF THE INVENTION

As embodied and broadly described herein, the present invention is directed to novel bacterial cultures and inoculums, and to methods of developing and using these strains. The bacteria of the present invention are thiocyanate-resistant and useful in the biooxidative pretreatment of refractory gold ores and other refractory ores. The use of such bacteria confers a number of technological advantages relating to improvements in operating flexibility, costs and environmental acceptability.

The economics of biooxidation processes are related to oxidation requirements. Biooxidation test work is aimed at determining the minimum amount of sulfide oxidation required in order to achieve acceptable metals extraction. The extent of sulfide oxidation is in turn dependent on the mineralogical composition of the material to be treated and the relative distribution of the associated metal values.

For example, the gold in refractory gold ores or concentrates often occurs as a colloidally dispersed phase within an arsenopyrite or arsenian matrix. In this case, complete destruction of the arsenopyrite matrix is generally required to recover the gold. However, gold also commonly occurs as micron-sized particles along the grain boundaries and interstices within pyrite, in which case it is generally more accessible. Depending on the mineralogy and gold distribution, acceptable gold recoveries are usually obtained at total sulfide oxidation levels of somewhat less than 100%.

However, at these lower oxidation levels, sulfur and other intermediate sulfur compounds can form, which react with cyanide to form thiocyanate. These compounds include sulfur, polymeric sulfur, sulfite, thiosulfate, and polythionates. Further, it has been found that the bacteria generate an extracellular capsule of colloidal sulfur, which the bacteria use as a store of metabolic energy. Also, the bacteria produce the enzyme rhodanese, which is employed in their internal metabolic pathways, that catalyzes the production of thiocyanate through the formation of an intermediate rhodanese-sulfur complex.

In biooxidation processes, these deleterious compounds, and, to a large extent, the bacteria, are removed before cyanidation by either rinsing with water or by washing in a counter current decantation circuit. Because the washing step is never 100% efficient, a small but significant portion of these materials report to the cyanidation process, resulting in generation of thiocyanate. This formation of thiocyanate in the gold recovery process is by far the largest consumer of cyanide and the primary source of thiocyanate.

Chemical reactions illustrative of the formation of sulfur, sulfur intermediates and thiocyanate in biooxidation-based gold extraction systems are indicated below.

A. Sulfur Oxidation Reactions Employed in Bacterial Biochemical Pathways $S^{2-}+3H_2O \rightarrow SO_3^{2-}+6H^++6e^-$ $S^0+O_2+H_2O \rightarrow SO_3^{2-}+2H^+$ $SO_3^{2-}+H_2O \rightarrow SO_4^{2-}+2H^+2e^-$ $2S_2O_3^{2-}+2e^- \rightarrow S_4O_6^{2-}+2e^-$ $2S_2O_3^{2-}+2e^- \rightarrow SO_3^{2-}+S^{2-}$ $S_4O_6^{2-}+H_2O \rightarrow SO_4^{2-}+S_2O_3^{2-}+2H^+$ $S_2O_3^{2-}+CN \rightarrow SO_3^{2-}+SCN^-$ B. Biooxidation and Chemical Attack of Sulfides $4Fe_7S_8+6SO_2+10H_2SO_4 \rightarrow 14Fe_2(SO_4)_3+10H_2O$ $Fe_7S_8+7Fe_2(SO_4)_3 \rightarrow 21FeSO_4+8S^0$ $4FeAsS + 5O_2 + 4H_2SO_4 \rightarrow 4HAsO_2 + 4FeSO_4 + 4S^0 + 2H_2O$ $CuFeS_2 + O_2 + 2H_2SO_4 \rightarrow CUSO_4 + FeSO_4 + 2S^0 + 2H_2O$ C. Inorganic Reactions Involving Sulfur $2S^{2-} + 3O_2 \rightarrow_2 SO_3^{2-}$ $2S^{2-} + 4SO_3^{2-} + 6H^+ \rightarrow 3S_2O_3^{2-} + 3H_2O$ $S^{2-} + 3SO_3^{2-} + 6H^+ \rightarrow 3S_4O_6^{2-} + 3H_2O$ $S^0 + SO_3^{2-} \rightarrow S_2O_3^{2-}$ $S_4O_6^{2-} + SO_3^{2-} \rightarrow S_2O_3^{2-} + S_3O_6^{2-}$ $S_4O_6^{2-} + S_2O_3^{2-} \rightarrow S_5O_6^{2-} + SO_3^{2}$ $4S_4O_6^{2-} + 6HO^- \rightarrow 5S_2O_3^{2-} + 2S_3O_6^2 + 3H_2O$ $2S_5O_6^{2-} + 6HO^- \rightarrow 5S_2O_3^{2-} + 3H_2O$ $S + CN^- \rightarrow SCN^-$ $2S_2O_3^{2-} + O_2\ 2CN^- \rightarrow 5SCN^- + 2SO_4^{2-}$ For complete oxidation, the sulfur is oxidized through to sulfate. However, at less than complete sulfide oxidation, there are a number of alternative routes by which thiocyanate can be generated in the system.

As noted, a number of intermediate oxidation products of sulfur are generated during biooxidation, particularly if oxidation is incomplete. Many of these compounds will react with cyanide in the gold extraction process to form thiocyanate. Thiocyanate is toxic to the bacteria conventionally employed in biooxidation at relatively low levels of between 5 ppm and 25 ppm. Consequently, tailings solution cannot currently be used with conventional bacterial strains upstream of the biooxidation process.

The bacteria used in biooxidation processes are generally referred to as aerobic, acidophilic, thermophilic, autochemolithotrophs; that is, they prefer warm acid and aerobic conditions in which to thrive and grow by metabolizing mineral substrates. The types employed in biooxidation fall into two broad categories: mesophiles and moderate thermophiles. Mesophilic cultures usually comprise a mixed consortium of *Thiobacillus ferrooxidans, Thiobacillus thiooxidans* and *Leptospirillum fenooxidans*. Moderate thermophiles usually comprise *Sulfobacillus thermosulfidooxidans, Metallosphera sedula* and bacteria of the sulfolobus type.

The present invention comprises a novel mixed culture of thiocyanate-resistant, mesophilic bacteria. This mixed culture is derived by inoculating a tail sample containing thiocyanate with a population of biooxidative bacteria. The population is cultured in a nutrient medium containing a concentration of solids. The solids concentration of the medium is sequentially increased and the bacteria cultured over a period of time in each concentration. OK medium is added to the media as needed to make up for evaporation losses. Finally, the adapted population of thiocyanate-resistant bacteria may be isolated or harvested to use as an inoculum in a biooxidation process.

Accordingly, one embodiment of the invention is directed to a method for isolating a thiocyanate-resistant bacterial culture comprising the steps of: inoculating a tail sample containing a concentration of thiocyanate with a population of biooxidative bacteria; culturing the population in a nutrient medium containing a first concentration of solids for a first period of time; increasing the solids concentration of the medium to a second concentration of solids and culturing the population for a second period of time; increasing the solids concentration of the medium to a third concentration of solids and culturing the population for a third period of time; and harvesting the population of bacteria.

In a preferred embodiment, the biooxidative bacteria comprise one or more species of bacteria selected from the group consisting of *T. Ferrooxidans, T. Thiooxidans* and *L. Ferrooxidans*, the *T. Ferrooxidans* 2,000 period of time is between 20 and 30 days, and the third period of time is between 10 and 20 days. The tail sample preferably comprises a pyritic concentrate that has been leached with cyanide for the recovery of gold. The initial thiocyanate concentration is preferably between 500 and 600 ppm. The nutrient media preferably comprises OK medium.

Still another embodiment is directed to bacteria isolated by the foregoing method. The bacterial strain of the present invention has a demonstrated tolerance to thiocyanate which is 23 times that reported elsewhere in the literature. Consequently, the bacteria of the present invention provide technological advantages in biooxidation processes including: improved operating flexibility, increased environmental acceptability, and operating cost reduction.

Gold can be leached in acidic thiocyanate solutions. The bacterial inoculum of the present invention, which is highly resistant to thiocyanate, allows an oxidation/co-extraction process based on thiocyanate. Such a process has major advantages over existing protocols, since the oxidation of sulfides and extraction of gold can be carried out simultaneously as opposed to sequentially as is the current practice. Such a process reduces capital costs by eliminating a step in the conventional process and lowers operating costs associated with the use of cyanide, lime, power and maintenance of environmental protection.

The oxidation potential required to oxidize gold metal to gold-I in thiocyanate solutions is about 600 mV and that required to reduce ferric ions is about 800 mV. This indicates ferric ions are a suitable oxidant for gold. Thiocyanate is thermodynamically unstable in acid media (pH of 1–3) but oxidation to cyanide and sulfate is extremely slow. Therefore, the conditions under which biooxidation is normally conducted are conducive to the extraction of gold by thiocyanate. The appropriate reactions are indicated below.

$Fe(SCN)_4^- + Au \rightarrow Fe^{2+} + Au(SCN)_2^- + 2SCN^-$ $3Fe(SCN)_4^- + Au \rightarrow 3Fe^{2+} + Au(SCN_4^- + 8SCN^-$ The gold thiocyanate complex can subsequently be recovered with either a strong base resin or carbon.

Ferric ions form strong complexes with thiocyanate, which at low concentrations can reduce the oxidizing potential of ferric and at the same time reduce the concentration of free thiocyanate. Optimal conditions for the extraction of gold by thiocyanate in biooxidative systems, in terms of concentration ranges, redox potential, pH and temperature are under investigation.

Accordingly, another embodiment is directed to a method for recovering a metal from a refractory ore comprising the steps of biooxidize the ore using the bacteria of the present invention, and leaching the metal in an acidic thiocyanate solution. In a preferred embodiment, the steps of biooxidize and leaching may occur substantially simultaneously. The pH of the solution is preferably from about 1 to about 3. The temperature of the solution is preferably from about 25° C. to about 70° C. The solution preferably has a concentration of thiocyanate of between about 1,000 and 2,000 ppm. The metal being recovered is preferably gold; however, as will be clear to those of ordinary skill in the art, the present invention can be used to recover other precious metals and materials such as nickel, copper and cobalt.

The following experiments are offered to illustrate embodiments of the invention and should not be viewed as limiting the scope of the invention.

EXAMPLES

Example 1

Adaptation of Inoculum

A mesophilic inoculum consisting of *T. Ferrooxidans, T. Thiooxidans* and *L. Ferrooxidans* was specially adapted to a flotation concentrate cyanidation tailing in preparation for amenability testing. The tailing comprised a pyritic concentrate that had already been leached with cyanide for the recovery of gold. The analysis of the material is indicated below.

| Component | Assay |
|---|---|
| Au | 7.69 gt$^{-1}$ |
| Ag | <200 gt$^{-1}$ |
| As | 2120 ppm |
| Hg | 493 ppm |
| Cu | 3457 ppm |
| Zn | 167 ppm |
| $S_T$ | 37.71% |
| $S^{2-}$ | 36.51% |
| $C_{org}$ | 0.03% |

Three different bacterial adaptations were conducted on unwashed tails MC-7), washed tails (MC-8) and acid washed tails (MC-9). Two tails samples were washed as thiocyanate contamination was anticipated. Thiocyanate is known to be toxic to the bacteria in the range of 5 ppm to 25 ppm. The adaptations were commenced with 2.5% solids in 9K nutrient medium.

Reactivation and adaptation of the bacteria proceeded slowly. However, all the adaptations showed a significant increase in ferric concentration and redox potential with a commensurate decrease in ferrous concentration in 55 to 60 days. The solids concentration was then increased to 5% for the MC-8 and MC-9 adaptations. OK medium was added with subsequent solids additions to make up for evaporation losses whereas water was used when not adding solids. At approximately 80 days, the inoculum was sufficiently active to permit increasing the solids content to 10% for the MC-8 and MC-9 adaptation and 5% for the MC-7 adaptation. At 125 days, the solids concentration was increased to 20% for the MC-8 and MC-9 in preparation for concentrate tails amenability testing and to 10% for the MC-7 adaptation. A summary of the adaptation results appears below.

| | MC-7 | MC-8 | MC-9 |
|---|---|---|---|
| 60 Days | | | |
| % Solids | 2.5 | 5.0 | 5.0 |
| Fe$^{3+}$ gl$^{-1}$ | 3.6 | 6.0 | 12.9 |
| Fe$^{2+}$ gl$^{1-}$ | 3.0 | <0.1 | <0.1 |
| mV° | 454 | 547 | 741 |
| SCN$^-$ ppm# | | | |
| 80 Days | | | |
| % Solids | 5.0 | 10.0 | 10.0 |
| Fe$^{3+}$ gl$^{-1}$ | 8.4 | 9.2 | 13.7 |
| Fe$^{2+}$ gl$^{1-}$ | <0.1 | <0.1 | <0.1 |
| mV° | 730 | 692 | 704 |
| SCN$^-$ ppm# | | | |
| 125 Days | | | |
| % Solids | 10.0 | 20.0 | 20.0 |
| Fe$^{3+}$ gl$^{-1}$ | 10.3 | 14.6 | 38.2 |
| Fe$^{2+}$ gl$^{1-}$ | <0.1 | <0.1 | 0.4 |
| mV° | 736 | 705 | 751 |
| SCN$^-$ ppm# | 571 | | |

*vs. Ag—AgCl electrode.
Determined by Dionex DX 500 HPLC ion chromatograph.

Back-up adaptations were implemented for each inoculum at 80 days. The back-up adaptations showed that the lag-phase (the time between inoculation with bacteria and the onset of bacterial oxidation as indicated by ferrous/ferric conversion and redox potential) had been reduced from 55–60 days to 20–30 days. This indicated that the bacteria continued to adapt and to thrive under conditions of high thiocyanate concentrations.

The results for the MC-7 adaptation on unwashed concentrate cyanidation tailings demonstrate a 23-fold improvement in thiocyanate tolerance over that reported elsewhere in the literature.

Other embodiments and uses of the invention will be apparent to those skilled in the art from consideration of the specification and practice of the invention disclosed herein. All documents referenced herein, including all U.S. patents, are specifically and entirely incorporated by reference. The specification and examples should be considered exemplary only with the true scope and spirit of the invention indicated by the following claims.

As is understood by those of ordinary skill in the art, variations and modifications of each of the disclosed embodiments can be made within the scope of this invention as defined by the following claims.

What is claimed is:

1. A method for isolating a thiocyanate-resistant bacterial culture comprising:

inoculating a tail sample containing a concentration of thiocyanate with a population of biooxidative bacteria;

culturing the population in a nutrient medium containing a first concentration of solids for a first period of time;

increasing the solids concentration of the medium to a second concentration of solids and culturing the population for a second period of time;

increasing the solids concentration of the medium to a third concentration of solids and culturing the population for a third period of time; and harvesting the population of bacteria.

2. The method of claim 1, wherein the biooxidative bacteria comprise one or more species of bacteria selected from the group consisting of *T. Ferrooxidans, T. thiooxidans* and *L. Ferrooxidans*.

3. The method of claim 1, wherein the biooxidative bacteria comprise *T. Ferrooxidans*.

4. The method of claim 1, wherein the first concentration is 2.5%.

5. The method of claim 1, wherein the second concentration is 10.0%.

6. The method of claim 1, wherein the third concentration is 20.0%.

7. The method of claim 1, wherein the first period of time is between 50 and 60 days, the second period of time is between 20 and 30 days and the third period of time is between 10 and 20 days.

8. The method of claim 1, wherein the tail sample comprises a pyritic concentrate that has been leached with cyanide for the recovery of gold.

9. The method of claim 1, wherein the concentration of thiocyanate is 500 and 600 ppm.

10. The method of claim 1, wherein the nutrient media comprises OK.

11. A method for recovering a metal from a refractory ore comprising the steps of: biooxidize the ore using the bacteria isolated by the method of claim 1, and leaching the metal in an acidic thiocyanate solution.

12. The method of claim 11 wherein the steps of biooxidation and leaching are carried out simultaneously.

13. The method of claim 11 wherein the pH of the solution is from about 1 to about 3.

14. The method of claim 11 wherein the temperature of the solution is 25° C.–70° C.

15. The method of claim 11 wherein the solution has a concentration of thiocyanate of between 1,000 and 2,000 ppm.

16. The method of claim 11 wherein the metal is gold.

* * * * *

UNITED STATES PATENT AND TRADEMARK OFFICE
CERTIFICATE OF CORRECTION

PATENT NO. : 6,379,919 B1
DATED : April 30, 2002
INVENTOR(S) : Carter, Andrew J.

It is certified that error appears in the above-identified patent and that said Letters Patent is hereby corrected as shown below:

Title page,
Item [73], Assignee, add the following:
-- [73] Assignee: Oxidor Corporation, Inc., Plano, Texas (US) --.

Signed and Sealed this

Twenty-fifth Day of February, 2003

JAMES E. ROGAN
*Director of the United States Patent and Trademark Office*